United States Patent

Jones et al.

[11] Patent Number: 5,409,492
[45] Date of Patent: Apr. 25, 1995

[54] SYSTEM FOR COUPLING AN IMPLANT TO A TOOL FOR INSERTING AND REMOVING THE IMPLANT

[75] Inventors: Scott A. Jones, Eighty Four; Thomas A. Mutschler; Gary Ferguson, both of Pittsburgh, all of Pa.

[73] Assignee: Stelkast Incorporated, Pittsburgh, Pa.

[21] Appl. No.: 103,863

[22] Filed: Aug. 9, 1993

[51] Int. Cl.⁶ .............................................. A61F 2/32
[52] U.S. Cl. .......................................... 606/86; 606/99
[58] Field of Search ................ 606/85, 53, 79, 84, 606/176, 80, 91, 104, 99, 100; 411/473

[56] References Cited

U.S. PATENT DOCUMENTS

| 924,999 | 6/1909 | Kummer . | |
|---|---|---|---|
| 2,634,641 | 4/1953 | Hodges . | |
| 3,585,994 | 6/1963 | Huggler . | |
| 3,995,323 | 12/1976 | Shersher . | |
| 4,305,394 | 12/1981 | Bertuch, Jr. . | |
| 4,306,550 | 12/1981 | Forte | 606/85 |
| 4,583,270 | 4/1986 | Kenna | 606/85 |
| 4,642,121 | 2/1987 | Keller . | |
| 4,716,894 | 1/1988 | Lazzeri et al. . | |
| 4,765,328 | 8/1988 | Keller | 606/85 |
| 4,919,679 | 4/1990 | Averill et al. . | |
| 4,921,493 | 5/1990 | Webb | 606/85 |
| 4,997,382 | 3/1991 | Berger . | |
| 5,064,427 | 11/1991 | Burkinshaw | 606/99 |
| 5,135,529 | 8/1992 | Paxson | 606/85 |
| 5,190,550 | 3/1993 | Miller | 606/85 |

FOREIGN PATENT DOCUMENTS 741869 6/1980 U.S.S.R. .

Primary Examiner—Michael A. Brown
Attorney, Agent, or Firm—Kirkpatrick & Lockhart

[57] ABSTRACT

The present invention provides a system for inserting and removing an implant comprising an implant and a tool. The implant has a protrusion, preferably triangular, extending from its proximal end. A tool designed for engaging the protrusion has a shaft, a sleeve and an actuation assembly. A cavity for receiving and lockingly engaging the protrusion on the implant is formed in the distal end of the shaft. The sleeve has a flattened surface in its interior configured to confront a complementary flattened surface on the shaft to constrain the shaft and the sleeve against rotation relative to each other. The actuation assembly moves the sleeve back and forth along the shaft to position the shaft into an extended position wherein the cavity is exposed or into a retracted position wherein the cavity, and the protrusion when it is seated in the cavity, are captured in the sleeve. A spring is provided in the actuation assembly for biasing the sleeve distally toward an open end of the shaft to move the shaft and the cavity in a normally retracted position within the sleeve.

19 Claims, 5 Drawing Sheets

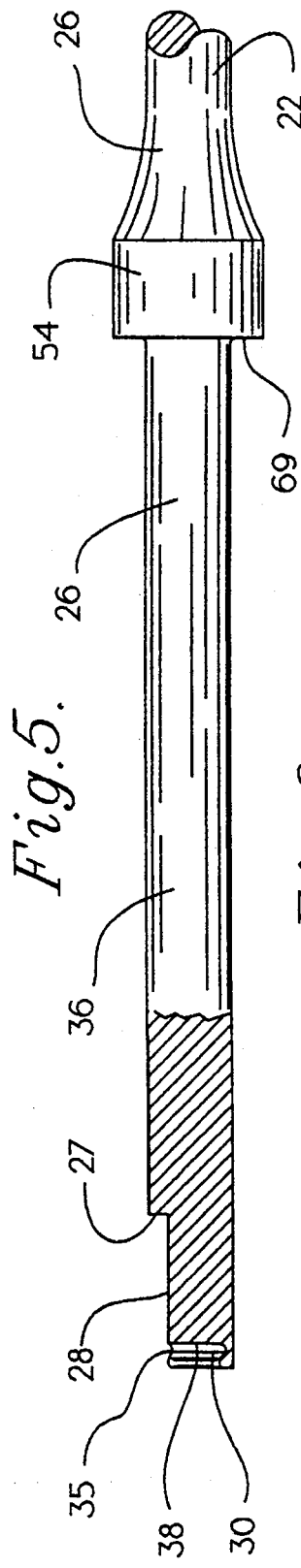
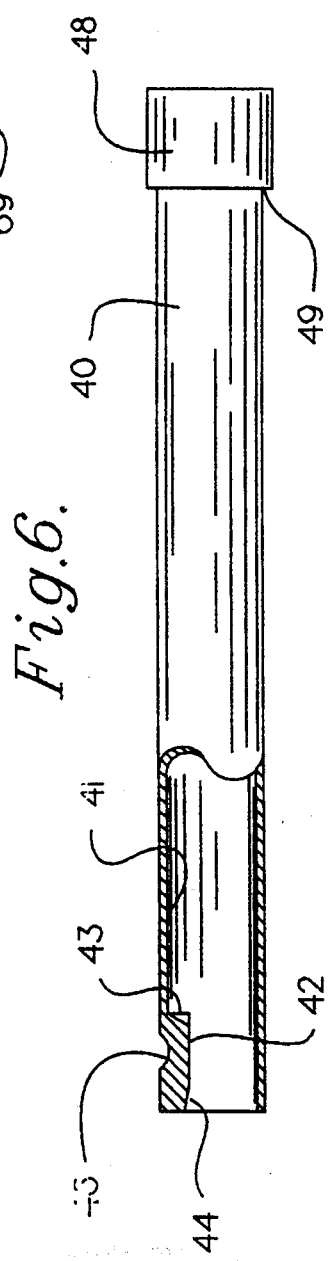
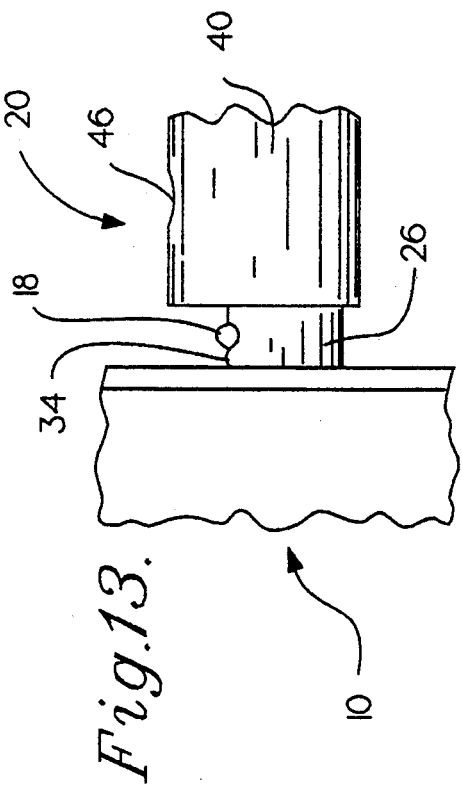
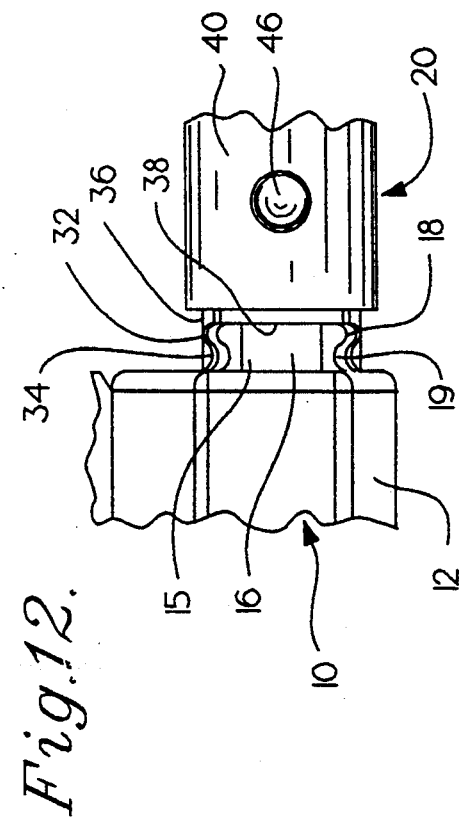
Fig.5.
Fig.6.
Fig.13.
Fig.12.

SYSTEM FOR COUPLING AN IMPLANT TO A TOOL FOR INSERTING AND REMOVING THE IMPLANT

BACKGROUND OF THE INVENTION

1. Field of the Invention

The present invention relates generally to surgical instruments and pertains, more specifically, to surgical instruments used in connection with the insertion and subsequent removal of implants.

2. Description of the Invention Background

The use of prosthetic devices to replace the natural joints of the body, either as a result of disease or injury to the natural joint, is commonplace. For example, in hip arthroplasty, it is necessary to replace the natural femoral head with a femoral implant having a stem portion which enters the medullary canal of the femur and another portion which provides an accurately located and securely held prosthetic head in place of the natural femoral head. To aid in the insertion of a femoral prothesis, tools are available that couple or grasp the prosthesis to enable the surgeon to manipulate the prosthesis for appropriate positioning during the procedure and to impact the prosthesis during implantation. The same tool or a different tool may be available for the subsequent extraction of the femoral prosthesis, if necessary. Prior to the insertion of the femoral implant, a broach is used to size the femoral canal. Typically, the broach is connected to its own tool to be grasped by the surgeon for manipulation during sizing of the femoral canal.

The most commonly used method of attaching a tool to an implant or broach is by complementary threads in the implant and the tool. A threaded hole is tapped in the implant itself. A matching threaded male portion on the instrument is screwed into the threaded hole, and the implant can then be manipulated. When the tool is removed, a cavity remains in the implant. A screw is sometimes used to fill the hole after the prosthesis is implanted. Even when screws are used, however, debris can collect in the cavity which can interfere with and even prevent the insertion of the male thread of the tool into the threaded hole of the implant. In addition, the collection of debris in the threads of tools create problems in maintaining clean tools and can make cleaning and sterilization of tools more time consuming.

In implant tools using threaded components, manufacturing of the internal threads can be very difficult and expensive in some materials, such as cobalt-chrome and titanium. The torque required for tapping these materials usually exceeds the capability of the material of the taps themselves, resulting in broken or dulled taps. Furthermore, insertion of the femoral implant into the femoral canal often requires impacting the tool with a mallet to drive the implant into the final position. Impacting the insertion tools can cause the threads to become slack or loose. This loosening can cause the surgeon to lose his feel for, and therefore sacrifice precision in, the proper seating of the implant in the femoral canal. Additionally, threaded instruments must be rotated approximately 3-10 revolutions to attach the instrument to the implant and another 3-10 revolutions to detach the instrument from the implant.

There is a need for a tool for use in inserting and removing both prostheses and broaches to reduce the number of tools a surgeon requires during an implant procedure. There is a further need for such a tool which eliminates cavities in the implant in which debris can accumulate. Finally, there is a need for a tool which can be connected and disconnected quickly to reduce the time for engaging a tool to an implant or a broach and the risk of infection associated therewith.

SUMMARY OF THE INVENTION

The present invention provides a system for inserting and removing an implant comprising an implant and a tool. The implant has a coupling member protruding from its proximal end. The coupling member has engaging surfaces thereon which are preferably angular in shape and more preferably, triangular. The coupling member is preferably a multi-sided protrusion with a neck and a head. At least a portion of the head extends outwardly beyond the neck of the coupling member. The tool is designed for manipulation of the implant and includes a cavity formed in the distal end thereof which is configured for complementary engagement with the engagement surfaces of the coupling member. Means are provided for moving the cavity into a first position for optionally receiving or releasing the coupling member and into a second position for locking the coupling member within the cavity when the coupling member is received within the cavity. Means are preferably provided for biasing the cavity in the second position.

More specifically, the preferred embodiment of the tool includes a distal end and a proximal end. The sleeve and the shaft members are positioned for slidable longitudinal movement relative to each other. The sleeve has an open distal end through which the distal end of the shaft and the cavity can pass between the first and second positions.

An advantage of the present invention is to provide a system for coupling an implant to a tool for inserting and removing the implant wherein no cavity remains in the implant to collect debris.

A further advantage of the present invention is to provide such a tool that reseats its connection with the implant after every blow of a mallet to prevent the implant from becoming loose, thereby improving the surgeon's feel for the precise seating of the implant in the femoral canal during insertion.

In addition, the insertion/extraction tool of the present invention can be used in combination with a broach as well as an implant. The use of one tool reduces the equipment costs and the time necessary to train operating room personnel.

The insertion/extraction tool of the present invention also reduces time in the operating room by increasing the speed with which the user can attach and detach the tool to broaches and implants. The present invention requires a turn of about one-quarter of a revolution of the actuation member on the insertion/extraction tool to attach or detach the tool from the implant.

BRIEF DESCRIPTION OF THE DRAWINGS

The present invention can be better understood by reference to the drawings wherein:

FIG. 5 is a side partial section view of the shaft member of the insertion/extraction tool of FIG. 1;

FIG. 6 is a side partial section view of the sleeve member of the insertion/extraction tool of FIG. 1;

FIG. 12 is a top view of the insertion/extraction tool in an extended position engaging the triangular protrusion of the implant;

FIG. 13 is a side view of the insertion/extraction tool in an extended position engaging the triangular protrusion of the implant;

DETAILED DESCRIPTION OF THE PREFERRED EMBODIMENTS

Figure 1:
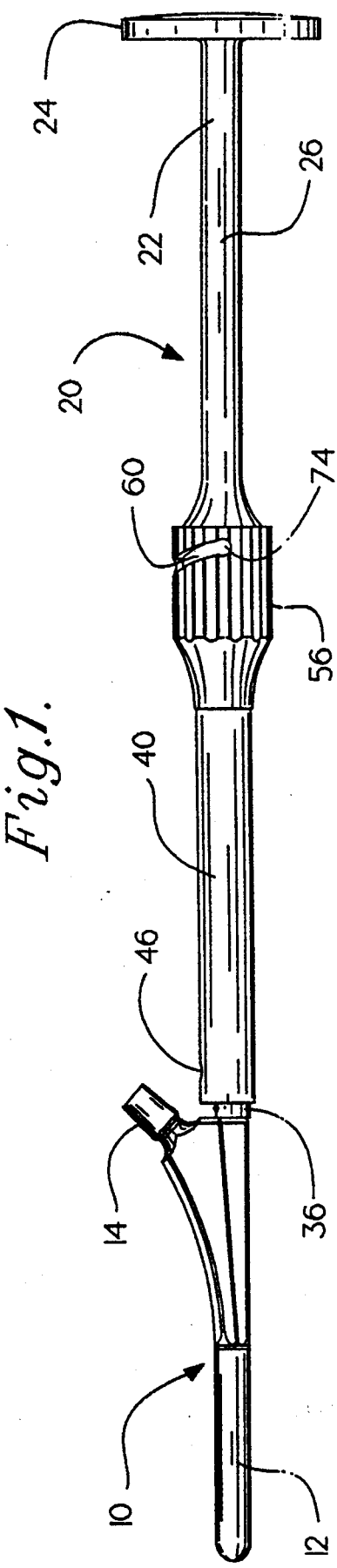
FIG. 1 is a side elevational view of the insertion/extraction tool connected to an implant.

FIGS. 1—15 illustrate the preferred embodiment of the system of the present invention for coupling an implant 10 to a tool 20 for manipulation of the implant 10 or any other suitably structured prosthetic device, broach or instrument. FIG. 1 shows the insertion/extraction tool 20 coupled to implant 10.

Figure 3:
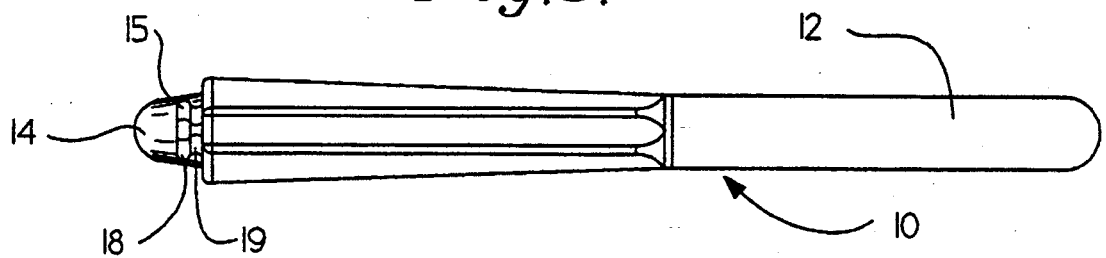
FIG. 3 is a view of the femoral implant of FIG. 2. rotated 90°.
Figure 2:
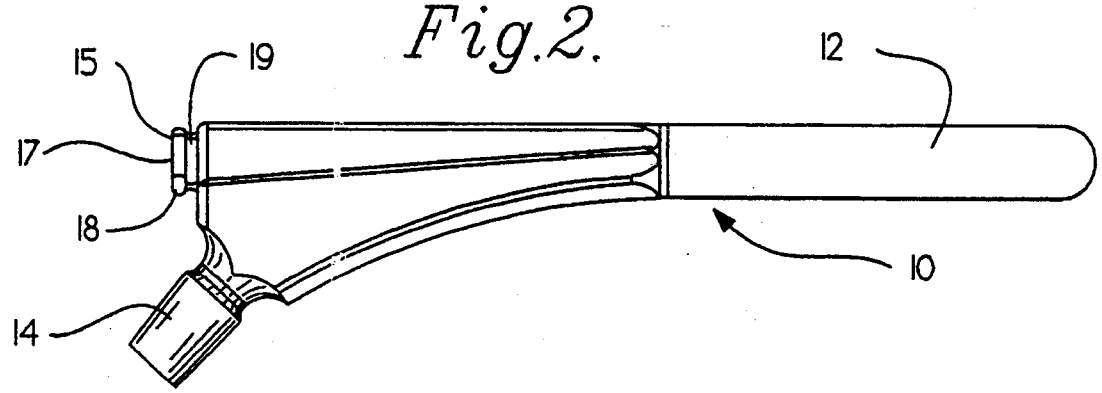
FIG. 2 is a side elevational view of a femoral implant with the triangular protrusion thereon.
Figure 4A:
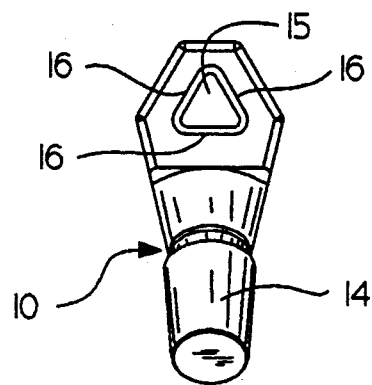
FIG. 4a—4d are end views of a femoral implant having variously shaped angular protrusions thereon.
Figure 4B:
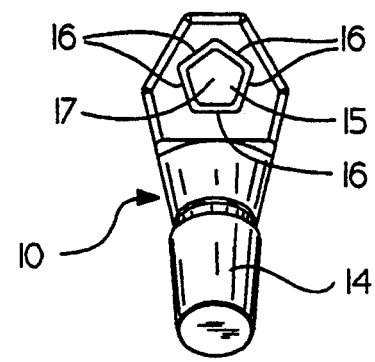
Figure 4C:
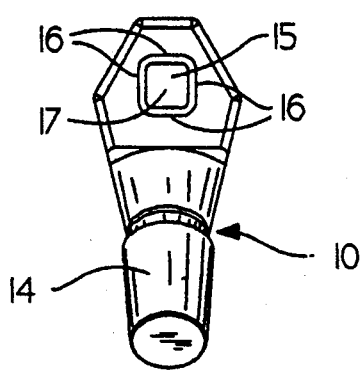
Figure 4D:
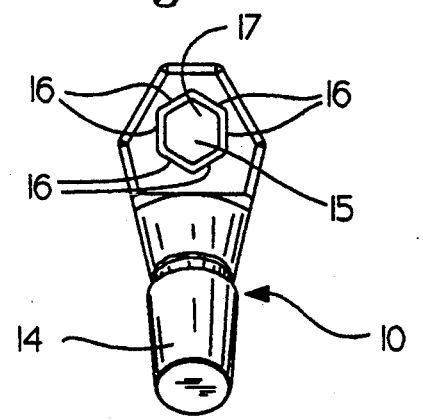

Femoral implant 10, as shown in FIGS. 2-4, has a stem 12, a neck 14 and a coupling member. The stem 12 is configured for placement into the medullary canal of a femur (not shown) that has previously been reamed and sized using a broach or other known instruments. Neck 14 fits into a separate femoral head component (not shown). The coupling member is shown in the form of a protrusion 15 which extends from the proximal end of implant 10. As shown in FIGS. 4a—4d, protrusion 15 can assume a variety of shapes, such as the triangular, square, pentagonal and hexagonal. Each protrusion 15 has surfaces 16 for engaging complementary surfaces on the tool 20, preferably including a neck 19 and head 18 curving upwardly from the neck 19 and leading to the generally flattened surface 17, together defining the perimeter of the protrusion 15. Although a variety of shapes will function to couple the implant 10 to the tool 20, including without limitation, regular, irregular, angled and curved shapes, the triangular protrusion 15 shown in FIG. 4a is preferred due to its simplicity and anti-rotational benefits.

Triangular protrusion 15 is formed integrally with femoral implant 10 of the same material by known methods such as casting or machining. The size of triangular protrusion 15 will be of appropriate proportion to the implant and the patient receiving the implant 10. Triangular protrusion 15 can also be formed on a broach used for sizing the opening in the femoral canal. Triangular protrusion 15 can then be grasped with the same insertion/extraction coupling tool 20 (FIG. 1) as is used with implant 10.

Insertion/extraction tool 20 generally includes a shaft member 26 with an impact head 24 attached to its proximal end, an actuation member, or knob 56 along its length and a sleeve member 40 at the distal end.

Figure 11:
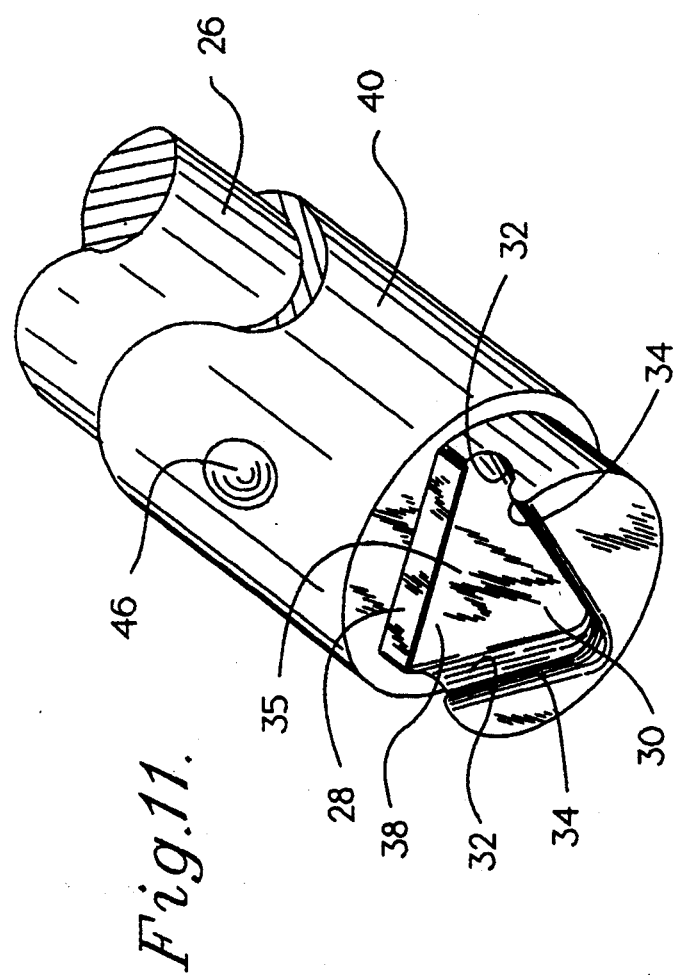
FIG. 11 is a perspective view of the distal end of the shaft member of the insertion/extraction tool, showing the partial cavity therein.

Referring to FIG. 5, shaft 26 has a proximal, exterior portion 22 and a distal interior portion 36 separated by shaft boss 54. The distal end of shaft 26, which is cylindrical along most of its length, has a reduced portion forming a step 27 and a planer surface 28. Cavity 30 is formed in the free distal end of the distal interior portion 36 of shaft 26 and is configured to complement and mate with the engaging side surfaces 16 of protrusion 15. The cavity 30, as shown in FIGS. 11—12 is configured for engagement with triangular protrusion 15 and has two walls 32 which complement the curved head 18 which defines the perimeter of triangular protrusion 15. Each wall 32 has formed in its interior a lip 34 which complements the sides 16 of neck 19 of protrusion 15. Finally, flattened surface 38 of cavity 30 is configured for confronting relationship with flattened surface 17 on protrusion 15. An opening 35 is provided in cavity 30 through which protrusion 15 can slide for entry into cavity 30.

Figure 7:
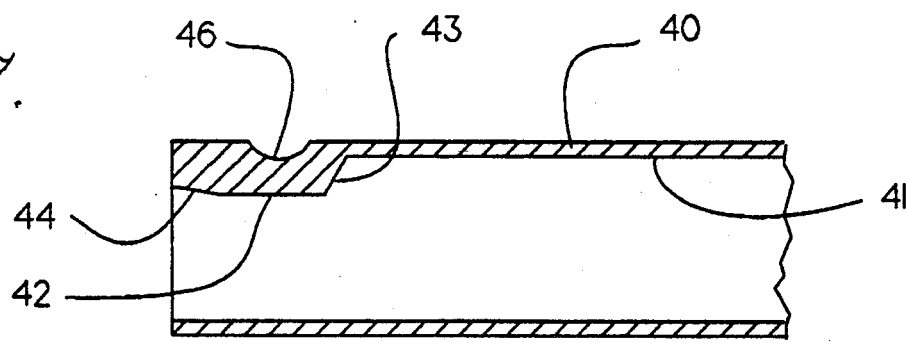
FIG. 7 is a cross-sectional close-up view of the distal end of the sleeve member of FIG. 6.
Figure 8:
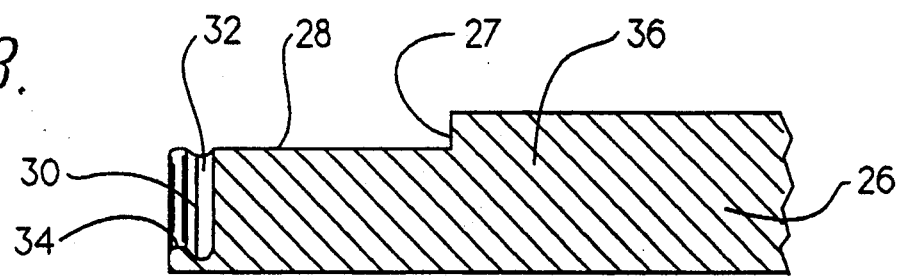
FIG. 8 is a cross-sectional close-up view of the distal end of the shaft member of FIG. 5.
Figure 15:
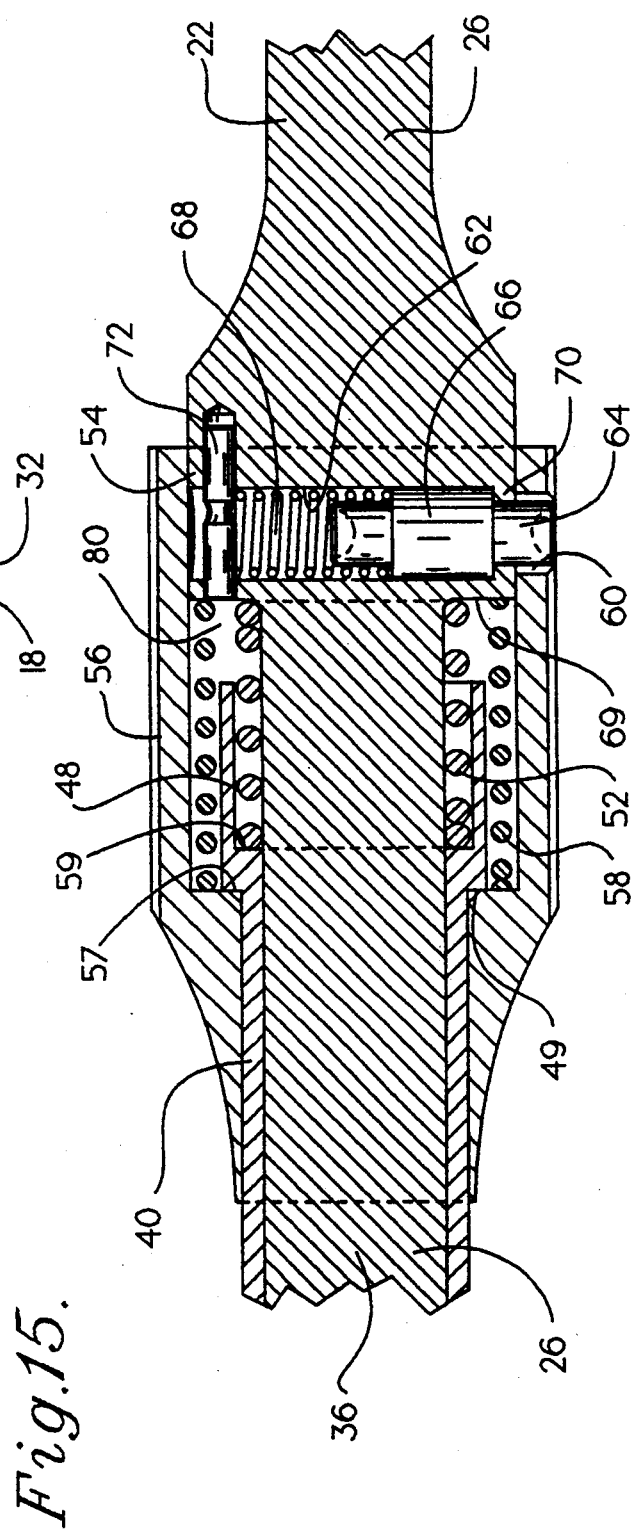
FIG. 15 is a cross-sectional view of the actuation assembly for biasing the sleeve member toward the distal end of the shaft member.

FIGS. 6, 7 and 15 show the features of sleeve 40. Sleeve 40 has sleeve boss 48 having an exterior shoulder 49 and an interior annular ledge or rim 59 near its proximal end. The interior surface 41 of sleeve 40 is cylindrical along most of its length and, as such, is configured for sliding movement relative to shaft 26. The top side of the hollow cylinder defined by the interior surface 41 has a thicker-walled, flattened portion 42 at the open distal end of sleeve 40 corresponding with planer surface 28 of shaft 26. A stop 43 is provided on one side of portion 42 which abuts the step 27 of shaft 26 to constrain shaft 26 against further extension. A bevel 44 is formed on the other side of portion 42 defining approximately a ten degree slope opening from the flat surface of portion 42 toward the open end of sleeve 40. Bevel 44 addresses tolerance stack up between head 18 of triangular protrusion 15 and flattened portion 42, thus ensuring a firm coupling between tool 20 and implant 10. A depression is formed on the top exterior surface of sleeve 40 to provide an indicator 46 to identify the location of the opening 35 in cavity 30.

Figure 9:
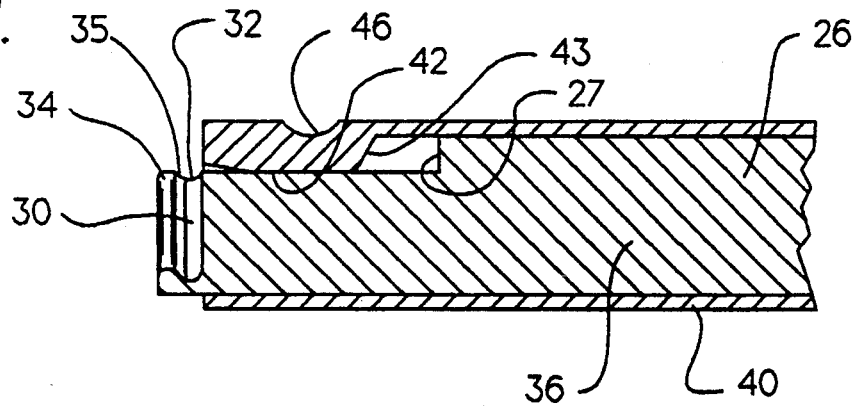
FIG. 9 is a cross-sectional close-up view of the distal end of the shaft member in an extended position relative to the sleeve member.
Figure 10:
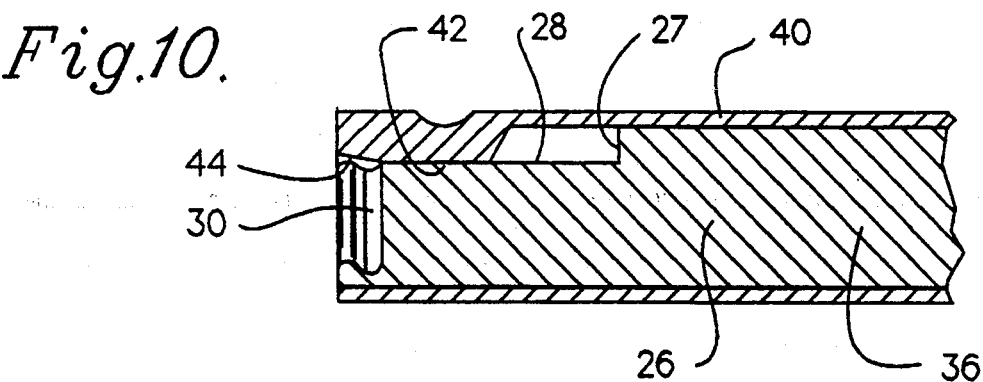
FIG. 10 is a cross-sectional close-up view of the distal end of the shaft member in a retracted position relative to the sleeve member.
Figure 14:
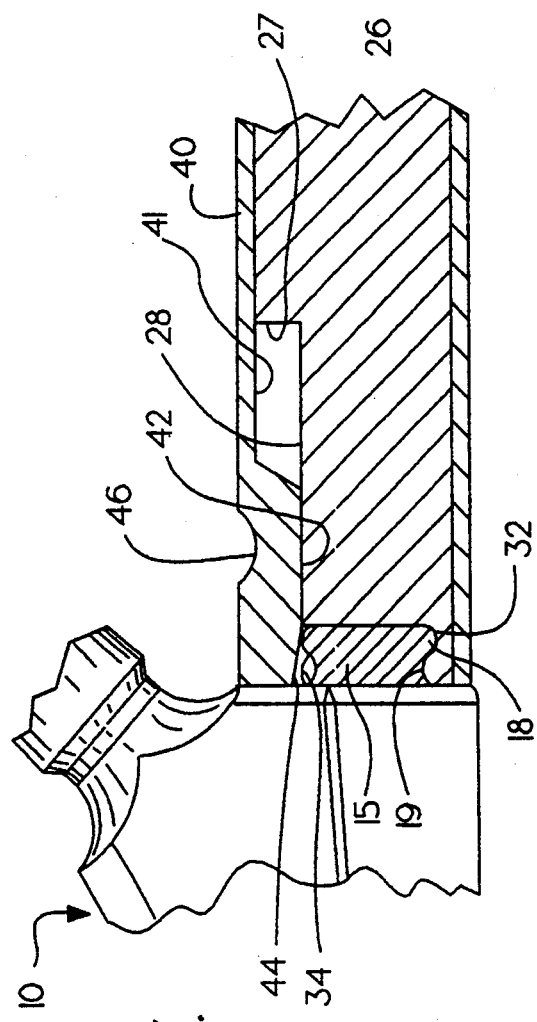
FIG. 14 is a view of the insertion/extraction tool in a retracted position following engagement of the shaft member to the protrusion on the implant.

FIGS. 9 and 10 show shaft 26 in extended and retracted positions, respectively, relative to sleeve 40. Shaft 26, is slidably received in sleeve 40 and planer surface 28 of shaft 26 is in a confronting relationship relative to flattened portion 42 of sleeve 40 to prevent rotation of shaft 26 within sleeve 40. FIGS. 9 and 12 illustrate shaft 26 in a first, extended position wherein cavity 30 extends out from sleeve 40 and is able to receive the protrusion 15 of implant 10. FIG. 10 illustrates shaft 26 in a second, retracted position wherein cavity 30 is positioned within sleeve 40 such that bevel 44 covers the open side 35 of cavity 30. As shown in FIG. 14, protrusion 15 is locked within cavity 30 when shaft 26 is retracted into sleeve 10. The end of shaft 26 is aligned to be coextensive with the end of sleeve 40 when in the retracted position.

The actuation assembly of the present invention is shown generally in FIG. 15. The actuation assembly includes knob 56, pin 64 and associated compression springs. Hollow cylindrical knob 56 surrounds a portion of the shaft boss 54 and the proximal end of sleeve 40 around boss 48 defining an annular chamber 80. Knob 56 has an interior annular rim 57 which abuts shoulder 49 of sleeve boss 48 acting as a stop to prevent sleeve 40 from sliding distally along interior portion 36 of shaft 26. As shown in FIG. 1, knob 56 has a spiral channel 60 formed in the wall thereof which extends approximately ninety degrees around knob 56. Knob compression spring 58 is housed in chamber 80. It axially surrounds sleeve boss 48 and is compressed between knob interior rim 57 and shoulder 69 of shaft boss 54 to constrain knob 40 against unnecessary movement when in use.

Sleeve boss 48 is positioned within chamber 80 and defines an annular cavity within chamber 80. Compression spring 52 axially surrounds the interior portion 36 of shaft 26 beneath the shoulder 69 of shaft boss 54 and is positioned in the annular cavity defined between sleeve boss 48 and the interior portion 36 of shaft 26. Spring 52 is compressed between the interior ledge 59 of sleeve boss 48 and the shoulder 69 of shaft boss 54 to bias sleeve 40 distally along interior portion 36 of shaft 26 to maintain shaft 26 in the retracted position. Compression spring 52 is of sufficient strength to deliver ample force to sleeve 40 to wedge the triangular protrusion 15 into triangular cavity 30 with bevel 44 to form a rigid coupling between the implant 10 and the implant tool 20.

Referring to FIG. 15, shaft 26 has a lateral bore 62 through shaft boss 54. Pin 64 is received within bore 62 and projects out of bore 62 past bore lip 70 a sufficient distance to engage the spiral channel 60 formed in the wall of knob 56. The top 74 of channel 60 is shown in FIGS. 1 and 15. The channel spirals down and around in a distal direction, preferably about a quarter of the distance around knob 56. Pin spring 68 biases pin boss 66 on pin 64 against bore lip 70 to retain pin 64 in bore 62. Retainer pin 72 retains pin spring 68 within lateral bore 62. Tool 20 can be assembled or disassembled by pressing pin 64 within bore 62. Knob 56 can then be moved over pin 64, and the components of tool 20 can then readily be taken apart.

Spiral channel 60 and pin 64 allow movement of sleeve 40 along the internal portion 36 of shaft 26. Compression spring 58 biases knob 56 distally into a normal, resting position wherein pin 64 is at the top end 74 of spiral channel 60 and sleeve 40 covers cavity 30. Pin 64 in spiral channel allows knob 56 to be rotated approximately ninety degrees from the resting position to an actuating position. When knob 56 is rotated, pin 64 rides in spiral channel 60, pulling knob 56 linearly along surface 55 of shaft boss 54. Because of the abutment of boss 57 with shoulder 49, the linear movement of knob 56 in the proximal direction pulls sleeve 40 proximally along interior portion 36 of shaft 26 as well. Sleeve compression spring 52 and knob compression spring 58 are overridden and compressed. The linear movement of sleeve 40 in the proximal direction along interior portion 36 of shaft 26 uncovers the opening 35 of cavity 30 (FIGS. 9 and 11) and places tool 20 in an open or extended position for receiving or releasing the protrusion 15, as needed. When knob 56 is released by the user, sleeve compression spring 52 and knob compression spring 58 force knob 56 and sleeve 40 distally along interior portion 36 of shaft 26 to enclose cavity 30 and place tool 20 in a closed or retracted position (FIG. 10) for capturing and locking protrusion 15 when it is within cavity 30 (FIG. 14). Pin 64 engages the top end 74 of spiral channel 60 to return knob 56 into its resting position and to maintain tool 20 in closed, retracted position.

In order to couple tool 20 to an implant 10, the protrusion 15 slides into cavity 30 through opening 35 when the interior portion 36 of shaft 26 is extended. FIGS. 12 and 13 show tool 20 engaged with implant 10 in an open or extended position. Interior portion 36 of shaft 26 extends from the open end of sleeve 40. Triangular protrusion 15 is seated on two sides within cavity 30 of shaft 26. Head 18 of protrusion 15 is seated against wall 32 of cavity 30 and wall lip 34 of cavity 30 is seated against side surfaces 16 of neck 19 of protrusion 15 in an interlocking relationship. The third side of triangular protrusion 15 is not interlocked. By releasing knob 56, sleeve 40 is allowed to move into the closed, retracted position. Sleeve 40 slides distally over the end of interior portion 36 to cover the third side of triangular protrusion 15, forcing bevel 44 of flattened portion 42 against the third side of neck 19 and head 18 so that triangular protrusion 15 is captured within cavity 30, thus creating a firm connection between implant 10 and tool 20.

To use the present invention, the surgeon will grasp exterior portion 22 of shaft 26 on the insertion/extraction tool 20 with one hand and twist knob 56 with the other hand in a counterclockwise direction from the resting position to the actuating position to slide sleeve 40 proximally along interior portion 36 of shaft 26 to extend cavity 30. Cavity 30 can then be coupled with triangular protrusion 15 by sliding face 17 of protrusion 15 over the flat surface 38 of cavity 30 and directing an apex of the triangle defined by the surfaces 16 of the head 18 and neck 19 of protrusion 15 toward and against the corresponding apex of the triangle cavity defined between walls 32 and wall lips 34 of cavity 30, respectively. The indicator, depression 46, is used to align tool 20 so that the opening 35 of cavity 30, when extended, will be faced in the desired direction. Knob 56 then is released to permit sleeve 40 to slide distally to the closed position. Bevel 44 then confronts the third side of triangular protrusion 15, and forces implant 10 into rigid, locking engagement with insertion/extraction tool 20. Implant 10 may be taken directly from storage packaging using tool 20, thus eliminating the need to touch implant 10. After coupling, implant 10 may then be inserted into the femoral cavity and manipulated to achieve the proper seating. Impact head 24, shown in FIG. 1, may be struck with a mallet if necessary for proper seating.

Insertion/extraction tool 20 has a minimum of number parts. All of the parts can be disassembled and reassembled easily, and can be made by known methods, such as casting and machining. Tool 20 is constructed in proportion to the implant 10 with which it is used, and is of a size allowing for comfort and ease of use with the hands with exterior portion 22 of shaft 26 preferably being long enough to function as a handle. The design and construction will withstand repeated use and heavy blows to impact head 24.

It is to be understood that the above detailed description of a preferred embodiment of the invention is provided by way of example only. Implants other than femoral implants may employ a protrusion 15 for coupling with the tool 20 of the present invention. Various details of design and construction may be modified without departing from the true spirit and scope of the invention as set forth in the appended claims.

What I claim is:

1. A system comprising:

an implant having a coupling member protruding from a proximal end thereof, said coupling member having engaging surfaces thereon;

a tool for manipulation of said implant, said tool having a shaft member having a distal end and a proximal end, a cavity formed in said distal end of said shaft configured for complementary engagement with said engaging surfaces of said coupling member, a sleeve member for receiving said shaft member, said sleeve member and said shaft member being positioned for slidable longitudinal movement relative to each other, said sleeve member having an open distal end through which said distal end of said shaft can pass between a first position for receiving and releasing said coupling member and a second position for locking said coupling member within said cavity when said coupling member is received within said cavity, said sleeve member having in the interior thereof adjacent said open end a locking surface, said locking surface being comprised of a planar surface having a bevel on one end thereof leading to said open end of said sleeve member and a stop on the opposite end thereof for limiting the longitudinal extension of said shaft member through said open end of said sleeve member; and an actuation assembly for moving said cavity between said first and said second positions;

wherein said cavity has at least one first surface for complementary engagement with at least one said engaging surface of said coupling member and an opening for passage of said coupling member to and from said cavity, said opening of said cavity is in said second position, thereby locking said coupling member within said cavity when said coupling member is received within said cavity.

2. The system recited in claim 1 further comprising means for biasing said cavity in said second position.

3. The system recited in claim 1 wherein said coupling member is comprised of a multi-sided protrusion having a neck and a head, said head having at least a portion thereof which extends outwardly from said neck.

4. The system recited in claim 3 wherein said multi-sided protrusion is triangular.

5. The system recited in claim 3 wherein said multi-sided protrusion is quadrilateral.

6. The system recited in claim 3 wherein said multi-sided protrusion is pentagonal.

7. The system recited in claim 3 wherein said multi-sided protrusion is hexagonal.

8. The system recited in claim 1 wherein said actuation assembly comprises:

an actuation member operatively connect to said shaft and operatively connect to said sleeve such that rotational movement of said actuation member from a resting position to an actuating position is translated into longitudinal sliding movement of said sleeve member along said shaft member; and means for biasing said actuation member in said resting position.

9. The system recited in claim 8 wherein movement of said actuation member from said resting position to said actuation position moves said cavity from said second position wherein said distal end of said shaft member is retracted within said sleeve member to said first position wherein said distal end of said shaft member is extended out of said open end of said sleeve member.

10. The system recited in claim 8 wherein said shaft member has a longitudinal axis and comprises an external proximal section, an internal distal section and a shaft boss intermediate said external and internal sections along said longitudinal axis, said internal section being positioned within said sleeve member, and said shaft boss having a bore therethrough transverse to said longitudinal axis of said shaft member.

11. The system recited in claim 10 wherein said sleeve member has a sleeve boss at a proximal end thereof generally adjacent said shaft boss surrounding and spaced from said external proximal section of said shaft to define a first annular chamber therebetween.

12. The system recited in claim 11 further comprising:

means positioned in said first annular chamber for biasing said sleeve member in the distal direction;

a pin member having a first portion captured with said bore and a second portion extending outwardly from said shaft boss;

said actuation member having a spiral channel formed therein for receiving said second portion of said pin, said actuation member being mounted on said shaft boss and about a segment of said internal distal section of said shaft member proximate said shaft boss and spaced from said sleeve boss to define a second annular chamber between said sleeve boss and said actuation member; and said means for biasing said actuation member toward said resting position is positioned in said second annular chamber.

13. The system recited in claim 12 wherein said means for biasing said sleeve member is a first compression spring and said means for biasing said actuation member is a second compression spring.

14. A tool comprising:

a shaft member having a first end and a second end, said first end having a cavity formed therein, said cavity having engaging surfaces configured for engagement with complementary engaging surfaces of a coupling member protruding from a device;

a sleeve member slidably mounted on said shaft member, said sleeve member having an open end, a hollow interior and a locking surface positioned in said interior adjacent said open end, said locking surface having a thicker-walled portion having a bevel formed at one end thereof leading to said open end and a stop at an opposite end thereof; and an actuation assembly for moving said engaging surfaces of said cavity into a first position for receiving and releasing said coupling member and into a second position for locking said coupling member when said coupling member is received within said cavity.

15. The tool recited in claim 14 further comprising means for biasing said sleeve member toward said first end of said shaft member.

16. The tool recited in claim 14 wherein said actuation assembly comprises:

a knob disposed circumferentially about a section of said shaft member and a section of said sleeve member defining an annular chamber between said knob and said sleeve and shaft members, said knob having a spiral channel formed therein;

a first spring disposed in said annular chamber for biasing said sleeve member toward said first end of said shaft member;

a second spring disposed in said annular chamber for biasing said knob toward a resting position wherein said cavity is in said second position;

a lateral bore formed in said shaft member;

a pin disposed in said bore and having one end thereof extending outwardly from said bore within said spiral channel;

a third spring disposed within said bore for biasing said pin toward said spiral channel to engage said knob.

17. A system comprising:

an implant having a coupling member protruding from a proximal end thereof, said coupling member having engaging surfaces thereon;

a tool for manipulation of said implant, said tool being comprised of:

a shaft member having a distal end, a proximal end and a cavity formed in said distal end of said shaft configured for complementary engagement with said engaging surfaces of said coupling member;

a sleeve member for receiving said shaft member, said sleeve member and said shaft member being positioned for slidable longitudinal movement relative to each other, said sleeve member having an open distal end through which said distal end of said shaft can pass between a first position for receiving and releasing said coupling member and into a second position for locking said coupling member within said cavity when said coupling member is received within said cavity; and an actuation assembly for moving said cavity between said first and second positions comprising:

an actuation member operatively connected to said shaft and operatively connected to said sleeve such that rotational movement of said actuation member from a resting position to an actuating position is translated into longitudinal sliding movement of said sleeve member along said shaft member; and means for biasing said actuation member in said resting position;

wherein said shaft member has a longitudinal axis and further comprises an external proximal section, an internal distal section and a shaft boss intermediate said external and internal sections along said longitudinal axis, said internal section being positioned within said sleeve member, and said shaft boss having a bore therethrough transverse to said longitudinal axis of said shaft member and wherein said sleeve member has a sleeve boss at a proximal end thereof generally adjacent said shaft boss surrounding and spaced from said external proximal section of said shaft to define a first annular chamber therebetween.

18. The system recited in claim 17 further comprising:

means positioned in said first annular chamber for biasing said sleeve member in the distal direction;

a pin member having a first portion captured with said bore and a second portion extending outwardly from said shaft boss;

said actuation member having a spiral channel formed therein for receiving said second portion of said pin, said actuation member being mounted on said shaft boss and about a segment of said internal distal section of said shaft member proximate said shaft boss and spaced from said sleeve boss to define a second annular chamber between said sleeve boss and said actuation member; and said means for biasing said actuation member toward said resting position is positioned in said second annular chamber.

19. The system recited in claim 18 wherein said means for biasing said sleeve member is a first compression spring and said means for biasing said actuation member is a second compression spring.

* * * * *